United States Patent
McElhone et al.

(10) Patent No.: US 10,327,073 B1
(45) Date of Patent: Jun. 18, 2019

(54) EXTERNALIZED AUDIO MODULATED BY RESPIRATION RATE

(71) Applicant: BOSE CORPORATION, Framingham, MA (US)

(72) Inventors: Dale McElhone, Marlborough, MA (US); Mikaela Alison Shannon, Newton Upper Falls, MA (US); Daniel Ross Tengelsen, Framingham, MA (US); Richard Eli Saffran, Southborough, MA (US); John Harlan Wendell, Boston, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 16/119,788

(22) Filed: Aug. 31, 2018

(51) Int. Cl.
  *A61B 5/08* (2006.01)
  *H04R 5/04* (2006.01)
  *A61M 21/00* (2006.01)
  *H04R 5/033* (2006.01)
  *H04S 7/00* (2006.01)
  *H04R 3/00* (2006.01)

(52) U.S. Cl.
  CPC .............. *H04R 5/033* (2013.01); *A61B 5/08* (2013.01); *H04R 3/00* (2013.01); *H04R 5/04* (2013.01); *H04S 7/304* (2013.01); *A61B 2562/0219* (2013.01); *A61M 2021/0027* (2013.01); *A61M 2021/0088* (2013.01)

(58) Field of Classification Search
  CPC .. A61M 2021/0027; A61M 2021/0088; A61B 2562/0219; A61B 5/08; H04R 1/028; H04R 5/033; H04R 5/04; H04R 3/00; H04S 7/304
  See application file for complete search history.

(56) References Cited

U.S. PATENT DOCUMENTS

| | | | | |
|---|---|---|---|---|
| 2014/0316192 | A1* | 10/2014 | de Zambotti | G06F 19/00 600/28 |
| 2016/0015315 | A1* | 1/2016 | Auphan | A61B 5/4815 600/301 |
| 2018/0078735 | A1* | 3/2018 | Dalgleish | A61B 5/6898 |
| 2018/0332424 | A1* | 11/2018 | Edry | H04S 7/30 |

* cited by examiner

*Primary Examiner* — Regina N Holder
(74) *Attorney, Agent, or Firm* — Patterson + Sheridan, LLP

(57) ABSTRACT

Aspects of the present disclosure provide methods, apparatuses, and systems for closed-loop respiration entrainment based on spatialized audio signals. According to an aspect, based on a determined rate of a subject's respiration, spatialization of a virtual sound source is altered to simulate a distance or directionality to the subject. Simulating the distance, directionality, and/or source characteristics comprises processing sounds of the virtual sound source to generate a perception of the sounds being heard from one or more distances or directions with reference to the subject. The altered virtual sound source attempts to regulate the rate of respiration of the subject. An audio device outputs the sounds of the altered virtual sound source.

20 Claims, 3 Drawing Sheets

EXTERNALIZED AUDIO MODULATED BY RESPIRATION RATE

BACKGROUND

Aspects of the present disclosure generally relate to methods, devices, and systems for using spatialization to affect a subject's respiration rate.

Respiration entrainment encourages a subject to breathe at a certain rate. One method for respiration entrainment includes open-loop respiration entrainment wherein a modulated sound is played in an effort to encourage a subject to breathe with the modulations. As an example, a modulated "back and forth" type of sound encourages the subject to inhale and exhale with the modulations in an effort to slow the subject's respiration rate. Additional methods, devices, and systems to help respiration entrainment are desirable.

SUMMARY

All examples and features mentioned herein can be combined in any technically possible manner.

Certain aspects provide a method for respiration entrainment of a subject. The method comprises determining a rate of respiration of the subject, altering, based on the determined rate of respiration, a spatialized location of a virtual sound source to simulate a distance or directionality to the subject, wherein simulating the distance or directionality comprises processing sounds of the virtual sound source to generate a perception of the sounds being heard from one or more distances or directions with reference to the subject, wherein the altered virtual sound source attempts to regulate the rate of respiration of the subject, and outputting the sounds of the altered virtual sound source.

According to aspects, the method further comprises tracking relative movement between the subject and the virtual sound source. The altering is further based on the tracked relative movement.

According to aspects, the method further comprises after outputting the sounds of the altered virtual sound source, determining an updated rate of respiration of the subject, and re-altering the spatialization of the virtual sound source based, at least in part, on the updated rate of respiration, to simulate direction or directionality to the subject, wherein simulating the direction or directionality comprises processing sounds of the virtual sound source to generate a perception of the sounds being heard from one or more distances or directions with reference to the subject, wherein the re-altered virtual sound source attempts to regulate the updated rate of respiration of the subject. The method further comprises outputting the sounds of the re-altered virtual sound source.

According to aspects, altering the spatialization of the virtual sound source comprises processing the virtual sound source using one or more directional filters. According to aspects, determining the rate of respiration comprises sensing the rate of respiration using at least one biosensor.

According to aspects, altering the spatialization of the virtual sound source comprises assisting the subject to visualize when to inhale and when to exhale. According to aspects, assisting the subject to visualize when to inhale and when to exhale comprises processing the sounds of the virtual sound source to generate sounds having a perception of location associated with a first side of the subject's body to encourage the subject to inhale and processing the sounds of the virtual sound source to generate sounds having a perception of location associated with a second side of the subject's body to encourage the subject to exhale. Outputting the sounds of the altered virtual sound source comprises outputting the generated sounds having a perception of location associated with a first side of the subject's body to slow the subject's rate of inhaling and outputting the sounds having a perception of location associated with a second side of the subject's body to slow the subject's rate of exhaling.

According to aspects, assisting the subject to visualize when to inhale and when to exhale comprises processing the sounds of the virtual sound source to generate sounds having a perception of location associated within a the subject's body to encourage the subject to inhale and processing the sounds of the virtual sound source to generate sounds having a perception of location outside the subject's body to encourage the subject to exhale. Outputting the sounds of the altered virtual sound source comprises outputting the generated sounds having a perception of location associated within the subject's body to slow the subject's rate of inhaling and outputting the sounds having a perception of location having a perception of location outside the subject's body to slow the subject's rate of exhaling.

According to aspects, altering the spatialization of the virtual sound source comprises processing the sounds of the virtual sound source to generate spatialized sounds and unspatialized sounds. Outputting the sounds of the virtual sound source comprises fading between outputting the generated spatialized sounds and the generated unspatialized sounds to regulate the rate of respiration of the subject.

According to aspects, outputting the sounds comprises outputting the sounds in at least one headphone of a headset worn by the subject. In an aspect, the sounds are output by an external device or a combination of the headphone and the external device.

Certain aspects provide an apparatus comprising an electroacoustic transducer, at least one biosensor in a first earpiece for determining a rate of respiration of a subject, a wireless communication unit, a memory, and a processor. The processor is configured to alter, based on the determined respiration rate, a spatialization of a virtual sound source to simulate distance or directionality to the subject, wherein simulating the distance or directionality comprises processing sounds of the virtual sound source to generate a perception of the sounds being heard from one or more distances or directions with reference to the subject, wherein the altered virtual sound source attempts to regulate the rate of respiration of the subject, and output the sounds of the altered virtual sound source.

According to aspects, the sounds of the virtual sound source comprise a soundscape relating to a place, and the wireless communication unit is configured to wirelessly access the soundscape from a library of soundscapes.

According to aspects the biosensor is configured to periodically re-detect the subject's rate of respiration and the processor is configured to re-alter the spatialization of the virtual sound source based, at least in part, on the re-detected rate of respiration, to simulate directionality to the subject, wherein simulating the directionality comprises processing sounds of the virtual sound source to generate a perception of the sounds being heard from one or more distances or directions with reference to the subject, wherein the re-altered virtual sound source attempts to regulate the re-detected rate of respiration of the subject.

According to aspects, outputting the sounds of the altered virtual sound source comprises fading between outputting the sounds in the first earpiece and a second earpiece of the apparatus.

According to aspects, altering, based on the determined respiration rate, a spatialization of a virtual sound source to simulate distance and directionality to the subject comprises altering a perceived angle of the sounds of the virtual sound source.

According to aspects, altering the spatialization of the virtual sound source comprises processing the sounds of the virtual sound source to generate spatialized sounds and unspatialized sounds and outputting the sounds of the virtual sound source comprises fading between outputting the generated spatialized sounds and the generated unspatialized sounds to regulate the rate of respiration of the subject.

Certain aspects provide a wearable audio device, comprising at least one processor configured and a memory coupled to the at least one processor. The at least one processor is configured to determine a rate of respiration of a subject, alter, based on the determined rate of respiration, a spatialization of a virtual sound source to simulate distance or directionality to the subject, wherein simulating the distance or directionality comprises processing sounds of the virtual sound source to generate a perception of the sounds being heard from one or more distances or directions with reference to the subject, wherein the altered virtual sound source attempts to regulate the rate of respiration of the subject, output the sounds of the altered virtual sound source, determine an updated rate of respiration after outputting the sounds of the altered virtual sound source, re-alter, based on the updated rate of respiration, the spatialization of the virtual sound source in an effort to regulate the updated rate of respiration, and output sounds associated with the re-altered spatialization of the virtual sound source.

According to aspects, the at least one processor is configured to track relative movement between the subject and the virtual sound source and the altering is further based on the tracked relative movement.

According to aspects, the wearable audio device comprises a first and a second earpiece, and outputting the sounds of the altered virtual sound source comprises fading between outputting the sounds in the first earpiece and the second earpiece of the wearable audio device.

According to aspects, the wearable audio device comprises an inertial motion unit (IMU), wherein the determined rate of respiration is based on signals collected via the IMU.

Advantages of the externalized audio modulated to affect respiration rate described herein will be apparent from the description and the claims.

DETAILED DESCRIPTION

Figure 1:
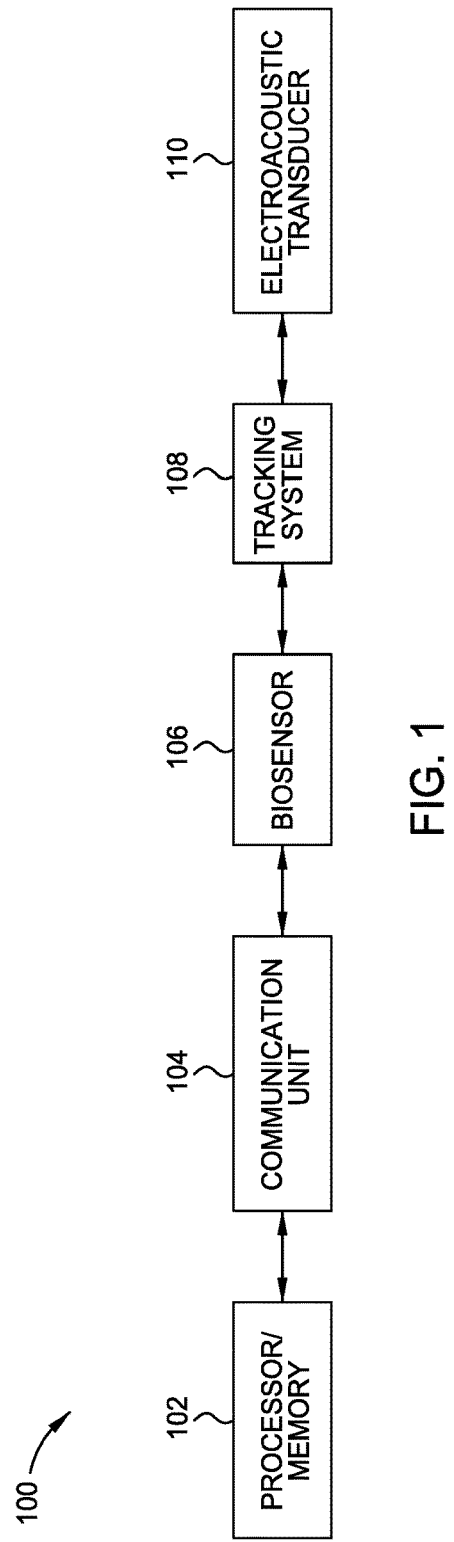
FIG. 1 illustrates an example headphone.

Aspects of the present disclosure provide methods, devices, and systems to spatialize respiratory entrainment. A device may sense, determine, or calculate a subject's respiration rate. Based, at least in part on the subject's respiration rate, audio presented to the subject is altered to affect the subject's respiration rate. The externalized audio modulated based, at least in part, on the subject's respiration rate encourages the subject to match his breathing with the received audio.

The audio may be altered by simulating a change in one or more of direction and distance of a virtual sound source to generate a perception of the sounds being heard from one or more distances or directions with reference to the subject. The altered virtual sound source attempts to regulate the rate of respiration of the subject.

As used herein, a virtual sound source corresponds to a physical location in the real-world environment surrounding a subject which is perceived as a location from which sound radiates, but at which no sound is actually produced by an object. In other words, the methods, devices, and systems described herein simulate a virtual sound source as if it were a real object producing a sound at the corresponding location in the real world. By changing perceived direction and distance of the sound, a subject is guided to match his respiration rate to the spatialized sounds.

The closed-loop entrainment described herein determines the subject's rate of respiration and outputs, for example, modulated sounds at a rate slower than the subject's rate of respiration. The modulated sounds are altered or processed to appear to the subject to come from at least one of different directions or distances at different times. The combination of the sounds and change in at least one of direction and distance help guide the subject to match his inhaling and exhaling with the spatialized audio presented, thereby gently and naturally reducing the subject's respiration rate.

An example of a current method for respiration entrainment includes a subject hearing a beep that indicates the subject is to inhale or exhale. Repeatedly listening to beeps may not be pleasant to the subject. Additionally, a beep may not help a subject to visualize when to inhale and when to exhale.

In contrast, aspects of the present disclosure use a subject's respiration rate as a trigger for visualizing spatializing audio from a virtual sound source. The subject's perceived direction and/or distance of the audio intuitively and pleasantly disambiguate a cue for an inhale versus a cue for an exhale. Additionally, as will be illustrated in FIGS. 3 and 4, the spatialized sounds help a subject visualize a direction for his breath at a particular time.

Spatialized respiration entrainment described herein particularly helps regulate a respiration rate when a subject's eyes are closed. When a subject is sleeping, for example, the described spatialization provides effective, intuitive cues for visualizing when to breathe in and out. Additionally, emerging wellness products involve controlled breathing as an integral part of their function. As non-limiting example, devices aimed at mindfulness, physical fitness, and sleep assistance may benefit from audio cues to encourage subjects at a specific rate as described herein.

FIG. 1 illustrates example components of a headphone 100. A headphone refers to a device that fits around, on, or in an ear and that radiates acoustic energy into the ear canal. Headphones are sometimes referred to as earphones, earpieces, headsets, earbuds, or sport headphones, and can be wired or wireless. In an example, a wearable device may include the components of the headphone 100 and is configured to perform closed-loop respiration entrainment as described herein. Any or all of the components in FIG. 1 may be combined into multi-function components.

The memory 102 may include Read Only Memory (ROM), a Random Access Memory (RAM), and/or a flash ROM. The memory stores program code for controlling the memory and processor 102. The memory and processor 102 control the operations of the headphone 100.

The processor 102 controls the general operation of the headphone. For example, the processor 102 performs process and control for audio and, optionally, data communication. In addition to the general operation, the processor 102 alters a spatialization of a virtual sound source to simulate distance or directionality to the subject based on a subject's detected respiration rate. According to aspects, the spatialization algorithm resides in an offboard device such as an external bedside unit or a wireless device, such as a cellular phone. As described in more detail below, simulating the distance or directionality comprises processing sounds of the virtual sound source to generate a perception of the sounds being heard from one or more distances or directions with reference to the subject. The altered virtual sound source attempts to regulate the rate of respiration of the subject. The processor may alter sound using one or more filters to simulate a virtual sound source. The processor applies the one or more filters to fade between sounds having a different direction and/or distance to help respiration rate entrainment. The processor, in combination with the electroacoustic transducer 110 is configured to output the sounds of the altered virtual sound source.

The headphone 100 optionally includes a communication unit 104. The communication unit facilitates a wireless connection with one or more wireless devices or the Internet cloud. The cloud refers to the provision of scalable computing resources as a service over a network. The cloud allows computers and other electronic devices access virtual computing resources such as, for example, storage, data, and applications.

The communication unit 104 may include one or more wireless protocol engines such as a Bluetooth engine. While Bluetooth is used as an example protocol, other communication protocols may also be used. Some examples include Bluetooth Low Energy (BLE), Near Field Communications (NFC), IEEE 802.11, or other local area network (LAN) or personal area network (PAN) protocols. The headphone may receive audio files wirelessly via the communication unit 104. Additionally or alternatively, the communication unit 104 may receive information associated with the subject's respiration rate, obtained via a contactless sensor, one or more selected audio files obtained from a wireless device or the cloud, and/or a relative change in movement between the subject and a virtual sound source.

The headphone 100 optionally includes one or more biosensors 106 used to determine, sense, or calculate the respiration rate of a subject wearing the headphone 100. According to an example, the biosensor 106 is an inertial motion unit (IMU) including a tri-axial accelerometer, a tri-axial gyroscope, and a magnetometer. According to an aspect, the biosensor 106 is an accelerometer. The biosensor 106 may be any sensor configured to determine, sense, or calculate the subject's respiration rate.

According to another aspect, only one earpiece (ear tip, ear cup) of the headphone 100 includes the biosensor 106. In an aspect, neither earpiece includes a biosensor 106. Instead, a biosensor, not on the headphone, may remotely detect a nearby subject's respiration rate. The biosensor may be a contactless biosensor. The contactless biosensor is configured to report detected respiration rate information to the processor 102, for example, via the communication unit 104.

The headphone 100 may optionally include a tracking system 108 such as a local positional tracking system configured to track movement of the subject wearing the headphone. In an aspect, the tracking system is configured to track relative movement between the subject and one or more of the virtual sound sources. By tracking a relative change, for example, in direction or distance between the subject and a virtual sound source, spatialization of the sounds are updated such that seamless respiration entrainment occurs despite a subject's change in location or orientation. As described with reference to the biosensor 106, one, both, or none of the earpieces may include a positional tracking system 108.

The electroacoustic transducer 110 outputs audio signals, including spatialized audio signals, to the subject. The transducer 110 is not necessarily a distinct component. The transducer may output spatialized audio sounds to one earpiece at a time.

Figure 2:
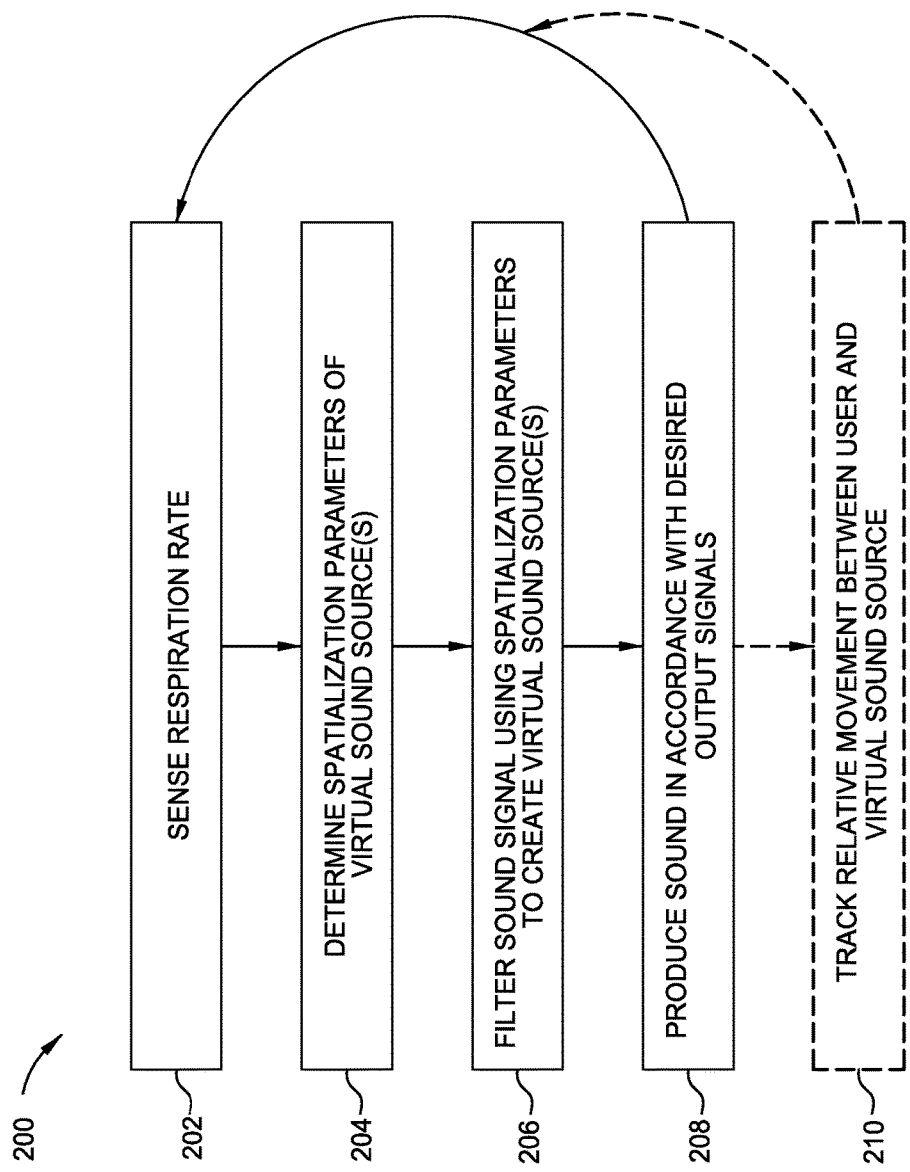
FIG. 2 illustrates an example flow diagram for spatializing audio to regulate a subject's respiration rate.

FIG. 2 illustrates example operations 200 to spatialize sound based on a subject's respiration rate. The method 200 may be performed by the headphone 100.

At 202, the headphone senses a subject's respiration rate. The headphone may determine the respiration rate based on information collected via one or more biosensors located on the headphone. According to an aspect, at 202, the headphone receives information associated with a subject's respiration. The information may be collected using one or more contactless sensors and wirelessly communicated to the headphone.

At 204, the headphone determines spatialization parameters of one or more virtual sound sources. The spatialization of a virtual sound source alters the subject's perception of the direction and/or distance of received sound signals. In certain aspects, the spatialization alters the perceived angle from which sound is received. The spatialized sounds provide cues to direct the subject to inhale and exhale, in an effort to regulate the subject's respiration rate.

At 206, the headphone filters sound signals using the determined specialization parameters to create one or more virtual sound sources. In one example, filters apply head related impulse responses (HRIRs) to an audio source to adjust a perceived direction and/or distance of generated sound. To simulate a virtual sound source at a specific angle relative to a subject, a mono audio source is filtered with HRIRs for a desired angle. Any angle can be simulated by interpolating HRIRs.

According to an aspect, the HRIRs are applied or sounds are otherwise processed to create a perception that the direction and/or distance of the sounds are moving over time. The perceived movement of sound provides cues for a subject to inhale and exhale to match the perceived movement of sound.

In an example, the sound is processed such that a virtual sound source generates sounds having a perception of location associated with a first side of the subject's body to encourage the subject to inhale and sound having a perception of location associated with a second side of the subject's body to encourage the subject to exhale.

The sounds output by the headphone alternates between sound that is perceived by the subject to be heard in one ear (a left ear), and then heard in another ear (right ear). Based on the determined respiration rate, the rate of delivered sounds having a perception of location associated with the first side (for example right side) of the subject's body slows the subject's rate of inhaling. Further, based on the determined respiration rate, the rate of delivered sound having a perception of location associated with the second side (for example left side) of the subject's body slows the subject's rate of exhaling. In an example, the headphone fades between outputting spatialized sounds located on each side of the subject's body.

According to another example, sounds output by the headphone alternate between sound that is perceived to be generated a location within the subject's body and sound that is perceived to be located outside of the subject's body. The headphone fades between outputting spatialized sounds located within and outside of the subject's body. Based on the determined respiration rate, the rate of delivered sounds having a perception of location within the subject's body slows the subject's rate of inhaling. Further, based on the determined respiration rate, the rate of delivered sound having a perception of location outside of the subject's body slows the subject's rate of exhaling.

According to another example, sounds output by the headphone alternate between sound that are spatialized and sounds that are not spatialized. The headphone fades between outputting spatialized sounds and outputting unspatialized sounds. Spatialized sounds may encourage a subject to exhale and unspatialized sounds may encourage a subject to inhale. Based on the determined respiration rate, the rate of delivered spatialized sounds slows the subject's rate of exhaling and the rate of delivered unspatialized sounds slows the subject's rate of inhaling.

The spatialization of sound enables closed-loop respiration entrainment. After delivery of sounds in accordance with the desired direction and/or distance, the closed-loop entrainment continues to 202 by sensing, determining, or calculating and updated respiration rate of the subject. The steps 204-208 continue until a desired respiration rate is reached. Accordingly, a subject's respiration rate is gradually reduced. In an aspect, once the subject achieves the desired respiration rate, the headphone continues to output spatialized sounds to maintain the respiration rate.

At 210, the headphone optionally tracks relative movement between the subject and the virtual sound source. When a subject physically moves or changes orientation, the spatialization parameters change to enable seamless entrainment.

According to one example, initially the spatialized sound alternates as perceived to be located to the left and at an angle of 30° relative to the subject and located to the right and at an angle of 30° relative to the subject. After entrainment has begun, the subject moves by standing up, walking, or rotating. By tracking relative movement between the subject and the virtual sound source, the spatialization parameters may be updated. Different filters may be selected to process audio such that the output signals continue to be perceived to alternate between a perception of location to the left and at an angle of 30° relative to the subject and a perception of location to the right and at an angle of 30° based on the subject's current location and position.

After producing sounds in accordance with desired spatialized output signals and the relative movement between the subject and the virtual sound source, the closed-loop entrainment continues to 202 by sensing, determining, or calculating and updated respiration rate of the subject. The steps 204-210 continue until a desired respiration rate is reached. In an aspect, once the subject achieves the desired respiration rate, the headphone continues to output spatialized sounds to maintain the respiration rate.

Figure 3:
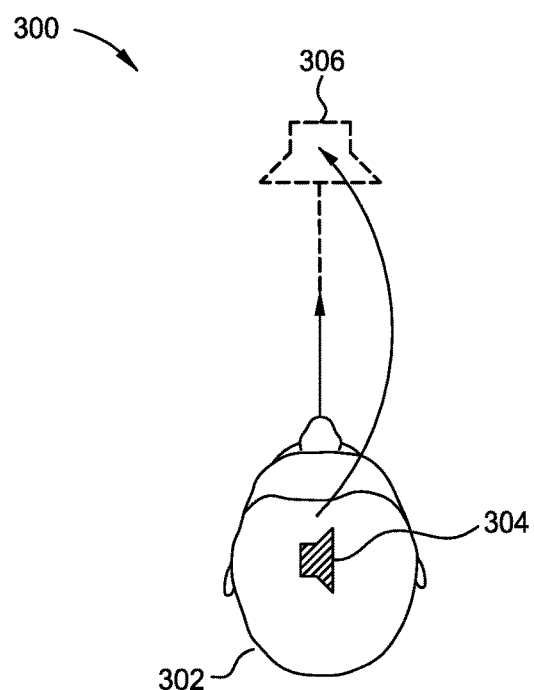
FIG. 3 illustrates an example of spatialized audio cues guiding the subject to inhale and exhale.

FIG. 3 illustrates an example of spatialized audio cues 300 guiding the subject to inhale and exhale. By altering the distance of the virtual sound source, sounds are perceived to alternate between a perception of location inside the subject's body and a perception of location outside of the subject's body.

Spatialized audio cues guide a subject 302 to inhale when receiving sound perceived to be located internally 304 or within the subject's body. Spatialized audio cues guide a subject to exhale when receiving sound perceived to be outside and in front of the subject's body 306. The headphone filters the sound signal to generate sound perceived by the subject to be located inside 304 the subject's body and outside 306 the subject's body. A subject may intuitively associate breathing in with sounds believed to be within the subject's body. Similarly, the subject may intuitively associate breathing out with sounds believed to be outside of the subject's body.

Figure 4:
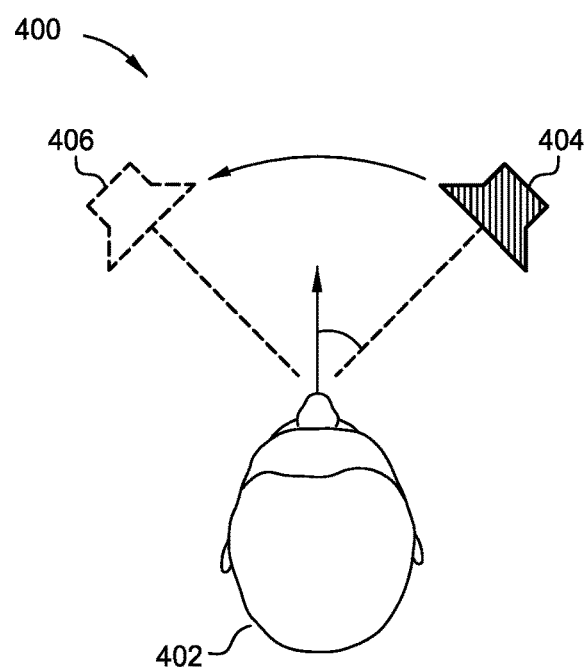
FIG. 4 illustrates an example of spatialized audio cues guiding the subject to inhale and exhale.

FIG. 4 illustrates an example of spatialized audio cues 400 guiding the subject to inhale and exhale. By altering the direction of the virtual sound source, sounds are perceived to alternate between a perception of location to the left of the subject's body and to the right of the subject's body.

Spatialized audio cues guide a subject 402 to inhale when receiving sound perceived to be located to the right 404 of the subject. The spatialized sounds 404 may be output by the right earpiece of an audio device. Spatialized audio cues guide a subject to exhale when receiving sound perceived to be to the left of the subject's body 406. The spatialized sounds 406 may be output by the left earpiece of the audio device. The headphone filters the sound signal to generate sound perceived by the subject to be located to the right 404 and to the left 406 of the subject. A subject may intuitively associate breathing in with sounds believed to be received from one side of the body and breathing out with sounds believed to be received from another of the body.

In an aspect, the spatialized entrainment illustrated in FIGS. 3 and 4 are combined with sounds to further cue the subject to breathe in and breathe out at the desired times. For example, a soundscape that is spatialized for respiration entrainment may sound like waves rolling in and waves rolling out. With reference to FIG. 3, the sound of waves rolling is spatialized to be perceived as being generated from within the subject's body 304. The sound of waves rolling back towards the ocean is spatialized to be perceived as being generated from outside and in front of the subject's body 306.

In another example, a soundscape that is spatialized for respiration entrainment may sound like a swinging hammock. With reference to FIG. 4, the sway of the hammock in one direction is spatialized to be perceived as being output on a left side of the subject's body. The sway of the hammock in the opposite direction is spatialized to be perceived as being output on a right side of the subject's body. In this manner, the type of audio that is spatialized enhances the spatialized entrainment by providing additional cues to signal to a subject when to breathe in and when to breathe out.

In an aspect, the headphone communicates with one or more external, out-loud units. The out-loud units, such as speakers, may be located at the subject's bedside. Spatialized sounds may alternate between the headphone and the bedside unit(s). In an aspect, the spatialized sounds alternate between two speakers on either side of the subject's bed. The alternating sounds provide cues to signal to the subject when to breathe in and when to breathe out.

In an aspect, the subject selects a desired soundscape for spatialized respiration entrainment. The subject may upload a preferred soundscape or select a preferred soundscape from the cloud or another device coupled to the headphone.

In an aspect, the subject selects the desired soundscape from a set of pre-configured options. Regardless, the subject has the option to select one of a several audio options based on personal preference which may further facilitate effectively slowing the subject's respiration rate.

In an aspect, in addition to modulating the location of the sound source, the spatialization algorithm controls the compactness or diffuseness of the virtual sound source to entrain respiration. The spatialization algorithm simulates shrinking of the virtual sound source or spreading out of the virtual sound source across a wider range of angles. The subject may associate breathing in with, for example, shrinking of the sound source and breathing out with, for example, spreading out the virtual sound source (or vice versa).

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

The invention claimed is:

1. A method for respiration entrainment of a subject comprising:
   determining a rate of respiration of the subject;
   altering, based on the determined rate of respiration, a spatialization of a virtual sound source to simulate a distance or directionality to the subject, wherein simulating the distance or directionality comprises processing sounds of the virtual sound source to generate a perception of the sounds being heard from one or more distances or directions with reference to the subject, wherein the altered virtual sound source attempts to regulate the rate of respiration of the subject; and
   outputting the sounds of the altered virtual sound source.

2. The method of claim 1, further comprising:
   tracking relative movement between the subject and the virtual sound source,
   wherein the altering is further based on the tracked relative movement.

3. The method of claim 1, further comprising:
   after outputting the sounds of the altered virtual sound source, determining an updated rate of respiration of the subject; and
   re-altering the spatialization of the virtual sound source based, at least in part, on the updated rate of respiration, to simulate direction or directionality to the subject, wherein simulating the direction or directionality comprises processing sounds of the virtual sound source to generate a perception of the sounds being heard from one or more distances or directions with reference to the subject, wherein the re-altered virtual sound source attempts to regulate the updated rate of respiration of the subject; and
   outputting the sounds of the re-altered virtual sound source.

4. The method of claim 1, wherein altering the spatialization of the virtual sound source comprises:
   processing the virtual sound source using one or more directional filters.

5. The method of claim 1, wherein determining the rate of respiration comprises sensing the rate of respiration using at least one biosensor.

6. The method of claim 1, wherein altering the spatialization of the virtual sound source comprises:
   assisting the subject to visualize when to inhale and when to exhale.

7. The method of claim 6:
   wherein assisting the subject to visualize when to inhale and when to exhale comprises processing the sounds of the virtual sound source to generate sounds having a perception of location associated with a first side of the subject's body to encourage the subject to inhale and processing the sounds of the virtual sound source to generate sounds having a perception of location associated with a second side of the subject's body to encourage the subject to exhale,
   wherein outputting the sounds of the altered virtual sound source comprises outputting the generated sounds having a perception of location associated with a first side of the subject's body to slow the subject's rate of inhaling and outputting the sounds having a perception of location associated with a second side of the subject's body to slow the subject's rate of exhaling.

8. The method of claim 6,
   wherein assisting the subject to visualize when to inhale and when to exhale comprises processing the sounds of the virtual sound source to generate sounds having a perception of location associated within a the subject's body to encourage the subject to inhale and processing the sounds of the virtual sound source to generate sounds having a perception of location outside the subject's body to encourage the subject to exhale,
   wherein outputting the sounds of the altered virtual sound source comprises outputting the generated sounds having a perception of location associated within the subject's body to slow the subject's rate of inhaling and outputting the sounds having a perception of location having a perception of location outside the subject's body to slow the subject's rate of exhaling.

9. The method of claim 1,
   wherein altering the spatialization of the virtual sound source comprises processing the sounds of the virtual sound source to generate spatialized sounds and unspatialized sounds, and
   wherein outputting the sounds of the virtual sound source comprises fading between outputting the generated spatialized sounds and the generated unspatialized sounds to regulate the rate of respiration of the subject.

10. The method of claim 1, wherein outputting the sounds comprises:
    outputting the sounds in at least one headphone of a headset worn by the subject.

11. An apparatus comprising:
    an electroacoustic transducer;
    at least one biosensor in a first earpiece for determining a rate of respiration a subject;
    a wireless communication unit;
    a memory; and
    a processor,
    wherein the processor is configured to:
        alter, based on the determined rate of respiration, a spatialization of a virtual sound source to simulate distance or directionality to the subject, wherein simulating the distance or directionality comprises processing sounds of the virtual sound source to generate a perception of the sounds being heard from one or more distances or directions with reference to the subject, wherein the altered virtual sound source attempts to regulate the rate of respiration of the subject; and output the sounds of the altered virtual sound source.

12. The apparatus of claim 11,
wherein the sounds of the virtual sound source comprise a soundscape relating to a place, and
wherein the wireless communication unit is configured to wirelessly access the soundscape from a library of soundscapes.

13. The apparatus of claim 11,
wherein the biosensor is configured to periodically re-detect the subject's rate of respiration, and
wherein the processor is configured to re-alter the spatialization of the virtual sound source based, at least in part, on the re-detected rate of respiration, to simulate directionality to the subject, wherein simulating the directionality comprises processing sounds of the virtual sound source to generate a perception of the sounds being heard from one or more distances or directions with reference to the subject, wherein the re-altered virtual sound source attempts to regulate the re-detected rate of respiration of the subject.

14. The apparatus of claim 11, wherein outputting the sounds of the altered virtual sound source comprises:
fading between outputting the sounds in the first earpiece and a second earpiece of the apparatus.

15. The apparatus of claim 11, wherein altering, based on the determined rate of respiration, a spatialization of a virtual sound source to simulate distance and directionality to the subject comprises altering a perceived angle of the sounds of the virtual sound source.

16. The apparatus of claim 11,
wherein altering the spatialization of the virtual sound source comprises processing the sounds of the virtual sound source to generate spatialized sounds and unspatialized sounds, and
wherein outputting the sounds of the virtual sound source comprises fading between outputting the generated spatialized sounds and the generated unspatialized sounds to regulate the rate of respiration of the subject.

17. A wearable audio device, comprising: at least one processor configured to:
determine a rate of respiration of a subject;
alter, based on the determined rate of respiration, a spatialization of a virtual sound source to simulate distance or directionality to the subject, wherein simulating the distance or directionality comprises processing sounds of the virtual sound source to generate a perception of the sounds being heard from one or more distances or directions with reference to the subject, wherein the altered virtual sound source attempts to regulate the rate of respiration of the subject;
and output the sounds of the altered virtual sound source;
determine an updated rate of respiration after outputting the sounds of the altered virtual sound source;
re-alter, based on the updated rate of respiration, the spatialization of the virtual sound source in an effort to regulate the updated rate of respiration; and
output sounds associated with the re-altered spatialization of the virtual sound source; and
a memory coupled to the at least one processor.

18. The wearable audio device of claim 17, wherein the at least one processor is configured to:
track relative movement between the subject and the virtual sound source,
wherein the altering is further based on the tracked relative movement.

19. The wearable audio device of claim 17, further comprising a first and a second earpiece, wherein outputting the sounds of the altered virtual sound source comprises:
fading between outputting the sounds in the first earpiece and the second earpiece of the wearable audio device.

20. The wearable audio device of claim 17, further comprising an inertial motion unit (IMU), wherein the determined rate of respiration is based on signals collected via the IMU.

* * * * *